United States Patent [19]

Kobayashi et al.

[11] Patent Number: 5,759,029

[45] Date of Patent: Jun. 2, 1998

[54] ESTHETIC ORTHONDONTIC WIRE

[75] Inventors: Masahiro Kobayashi, Funabashi; Fumio Watari, Sapporo; Toru Imai, Sapporo; Shinji Nakamura, Sapporo, all of Japan

[73] Assignees: Sun Medical Co., Ltd., Moriyama; Rocky Mountain Morita Corporation, Tokyo; Unitika Glass Fiber Co., Ltd., Uji, all of Japan

[21] Appl. No.: 718,952

[22] Filed: Sep. 26, 1996

Related U.S. Application Data

[63] Continuation-in-part of Ser. No. 709,320, Sep. 4, 1996.
[51] Int. Cl.$^6$ ..................................... A61C 7/20
[52] U.S. Cl. ............................................. 433/20
[58] Field of Search ................................. 433/20

Primary Examiner—Cary E. O'Connor
Attorney, Agent, or Firm—Ostrolenk, Faber, Gerb & Soffen, L.L.P.

[57] ABSTRACT

An esthetic orthodontic wire comprising a composite material which includes a biocompatible inorganic fiber and a thermoplastic resin. The inorganic fiber is glass fiber formed linearly continuous and having a generally circular or oval cross-sectional shape. The inorganic fiber has a diameter ranging from 1 to 100 μm. The biocompatible inorganic fiber is produced from a mixture of calcium oxide, diphosphorus pentoxide, silicon dioxide and aluminium oxide. The inorganic fiber is biocompatible, in which a molar ratio of calcium/phosphorus is within a range of from 0.5 to 3.0, wherein total of calcium oxide and diphosphorus pentoxide is within a range of from 20 to 65% by weight relative to the glass fiber, and total of silicon dioxide and aluminium oxide is within a range of from 35 to 80% by weight relative to the glass fiber. The content of the glass fiber is within a range of from 5 to 70% by volume of the orthodontic wire. The thermoplastic resin is one selected from the group consisting methylmethacrylate resin and a copolymer of methylmethacrylate and one of methacrylate and acrylate. Additionally, the orthodontic wire is generally white and translucent. The orthodontic wire has a light transmittance of not lower than 5% within a visible light region. The orthodontic wire has a residual deflection of not larger than 1 mm in a load-deflection behavior obtained under a test in which a distance between support points is 14 mm, and a flexural load is within a range of from 0.5 to 6.0 N.

14 Claims, 4 Drawing Sheets

ESTHETIC ORTHONDONTIC WIRE

This application is continuation-in-part of applicants' co-pending application filed Sep. 4, 1996 under Ser. No. 08/709,320.

BACKGROUND OF THE INVENTION

1. Field of the Invention

This invention relates to improvements in an orthodontic wire, and more particularly to an orthodontic wire which has excellent dynamic characteristics, biocompatibility and estheticity so that it does not exhibit unpleasant luster characteristic for metal as compared with conventional metal orthodontic wires, is white, translucent and excellent in estheticity, and refreshing in use, and hardly has a residual strain even under a continuously applied load so as to provide an optimum orthodontic force.

2. Description of the Prior Art

Hitherto in case of carrying out orthodontic cures such as adjustment of irregular occlusion in dental cures concerning adjustment of row of teeth, adjustment has been made under an elastic force of a metal wire as an orthodontic wire. In this connection, in order to move a tooth in cure, it is required to apply an orthodontic force (the optimum orthodontic force) which produces a pressure above a dental root film capillary blood pressure of about 15 g/cm2 and below 20 g/cm$^2$, onto the dental root film. The magnitude of the orthodontic force is required to be normally within a range of from 0.5 to 3 N. It is required to continuously apply a relatively low force in order to achieve an adjustment of teeth. Regeneration of bone gradually proceeds under application of such a low force, in which a tooth is moved inclined thereby achieving adjustment of row of teeth. According to conventional techniques, application of a predetermined outside force necessary for orthodontic cure is made by a metal wire. The metal wire is to be installed through a bracket formed of ceramic or metal wire so as to apply a pressure to the teeth from the outside or the inside of the row of teeth. The metal wire is made of a Co—Cr alloy or a Ni—Ti alloy.

Japanese Patent Provisional Publication No. 2-109552 discloses an invention relating to an orthodontic arch wire of a composite material of a single core cable (for optical communication) made of quartz glass and silicone resin. The arch wire of this Publication has a Young's modulus which is as low as about 1/10 of the Ni—Ti system wire, so that it is insufficient in mechanical characteristics and impact resistance. Accordingly, the arch wire can be used only in a limited period of curing. Japanese patent Provisional Publication No. 1-135345 discloses an invention relating to an orthodontic wire made of a reinforced plastic containing continuous fiber such as alumina fiber or glass fiber. The external appearance of the alumina fiber of this Publication is white and not transparent. The wire appears projecting when installed onto tooth because of being not transparent, and therefore is inferior in estheticity. The alumina fiber is a material which is inactive and stable, and therefore cannot be decomposed and absorbed in living body.

Additionally, it is taken into account to use a wire containing E, C, S, A glass fiber which is industrially used, as an orthodontic wire; however, such a wire has no biocompatibility.

The above-mentioned metal orthodontic wire has such defects that orthodontic effects unavoidably are reduced owing to a lowered orthodontic load due to fatigue characteristic for metal under repeated use and owing to residual permanent deformation. Additionally, the metal orthodontic wire is excessively high in elastic modulus and inferior in estheticity, and the patient always has the feeling of foreign matters in the mouth so as to be difficult to be used. Accordingly, detaching the orthodontic wire is often made by the patient, and therefore the effects of the orthodontic cure cannot be effectively made. Additionally, some of the metal orthodontic wire contains nickel and chromium and therefore it is not impossible to completely deny the noxiousness of them. Furthermore, the metal orthodontic wire exhibits unpleasant luster characteristic for metal and can be harmonized in color with natural teeth, so that the user or patient exhibits abnormal looks. Particularly when the user of the metal orthodontic wire is a female, she may have an unbearable feeling so that she often detach the metal orthodontic wire thereby suppressing the effects of orthodontic cure.

Moreover, the metal orthodontic wire affects the image pick-up operation for accomplishing an image inspection of CT (Computed Tomograph) and MRI (Magnetic Resonance Imaging). The CT image pick-up is accomplished as a step of an orthodontic cure on a patient who has a large deformation in jaws or a face. In case that the metal orthodontic wire is installed, a photograph image hindrance due to the metal (i.e., an artifact) inevitably occurs because of scattering of X-ray, and therefore a clear and accurate X-ray image cannot be obtained. The MRI image pick-up is accomplished in case of the patient who has symptoms in a jaw joint and a muscle of mastication, in which the metal orthodontic wire contains ferromagnetic materials such as Cr, Ni and Fe and therefore there occurs a disturbed local magnetic field thereby arising an artifact. As a result, a necessary image cannot be obtained like in the case of the CT. In view of the above, under the present status, an orthodontic apparatus including the orthodontic wire is temporarily detached from the teeth when the image pick-up operation is made, and it is again installed to the teeth when the image pick-up operation is completed. This requires troublesome operations of detaching and installing the orthodontic wire. Additionally, the patient is supplied with such a large load such as pain during detaching and time consumption.

Apart from the above, nowadays not only children during the growth period but also adults (particularly female adults) are highly interested in beauty culture concerning mouth and figure in connection with orthodontic cure. In this regard, the patients' requirements for obtaining highly esthetic orthodontic apparatuses which are transparent and not prominent are rapidly increasing.

SUMMARY OF THE INVENTION

An object of the present invention is to provide an improved esthetic orthodontic wire which can effectively overcome drawbacks encountered in conventional orthodontic wires.

Another object of the present invention is to provide an improved esthetic orthodontic wire which is excellent in biocompatibility and can completely meet recent patients' requirements for estheticity so as to be transparent or translucent and not prominent.

A further object of the present invention is to provide an improved esthetic orthodontic wire which is arranged to provide no fatigue even under repeated use and to be highly biocompatible so as to provide feeling of foreign matters to patients, in which the esthetic orthodontic wire is not required to be detached during CT and MRI image inspections, while providing satisfying feeling to the patients.

An esthetic orthodontic wire according to the present invention comprises a composite material including a biocompatible inorganic fiber(s), and a thermoplastic resin so that the wire is white and translucent, and excellent in estheticity. Additionally, preferable features of the esthetic orthodontic wire according to the present are discussed below. The biocompatible inorganic fiber is a fiber glass which is produced from a mixture of calcium oxide, diphosphorus pentoxide, silicon dioxide and aluminium oxide. The inorganic fiber is formed linearly continuous and has a generally circular or oval cross-sectional shape, in which the inorganic fiber has a diameter ranging from 1 to 100 μm. The inorganic fiber is biocompatible, in which a molar ratio of calcium/phosphorus is within a range of from 0.5 to 3.0, wherein total of calcium oxide and diphosphorus pentoxide is within a range of from 20 to 65% by weight relative to the glass fiber, and total of silicon dioxide and aluminium oxide is within a range of from 35 to 80% by weight relative to the glass fiber. Content of the glass fiber is within a range of from 5 to 70% by volume of the orthodontic wire. The orthodontic wire has a generally circular or oval cross-sectional shape and has a diameter or long diametrical dimension within a range of from 0.1 to 5.0 mm. The orthodontic wire has a diameter or long diametrical dimension within a range of from 0.3 to 2.0 mm. The orthodontic wire has a generally regular square or rectangle cross-section, wherein the orthodontic wire has a short side in cross-section, within a range of from 0.1 to 5.0 mm, and a long side in cross-section, within a range of from 0.2 to 10.0 mm. The orthodontic wire has a light transmittance of not lower than 5% within a visible light region. The thermoplastic resin is one selected from the group consisting of methylmethacrylate resin and a copolymer of methylmethacrylate and one of methacrylate and acrylate. The orthodontic wire has a residual deflection of not larger than 1 mm in a load-deflection behavior obtained under a test in which a distance between support points is 14 mm; a flexural load is within a range of from 0.5 to 6.0N.

Advantageous effects of the orthodontic wire according to the present invention will be discussed hereinafter.

First, the orthodontic wire according to the present invention is the same in color tone as natural teeth and high in biocompatibility, so that it does not provide reflection of unnatural light (made by conventional metal orthodontic wire) and an irritant feeling characteristic in metal. Accordingly, the orthodontic wire according to the present invention is refreshing in use and beautiful in external appearance, thus providing a high estheticity and an excellent feeling in use. Secondly, the orthodontic wire according to the present invention is smaller in coefficient of thermal conductivity than metal, and therefore no feeling of physical disorder due to temperature difference occurs even at a low outside temperature. Additionally, no galvanic current due to the action of volta cell is generated in use within the mouth of the patient, thereby making it possible to improve the feeling of the orthodontic wire in use. Thirdly, as the most important effects, the orthodontic wire according to the present invention has no residual strain or permanent set (which has been a defect of the conventional metal orthodontic wire) even against continuous repeated application of load of the orthodontic force, so that the substantial orthodontic effects come out within a relatively short period of time thereby providing a beautiful dental arch or row of teeth. Fourthly, it is possible to add a water-resistant component to the composite material of the glass fiber and acrylic resin. Additionally, it is also possible to form water-resistant and wear-resistant coatings or to make a coating treatment on the surface of the orthodontic wire from the point of view of estheticity. Fifthly, in case that the patient is required to be subjected to inspection of MRI or CT, the orthodontic wire according to the present invention does not disturb the image of MRI (Magnetic Resonance Imaging) or CT (Computed Tomograph) and therefore is not required to be detached and installed thereby avoiding troublesome installation and detaching operations thereof.

DETAILED DESCRIPTION OF THE INVENTION

Figure 1:
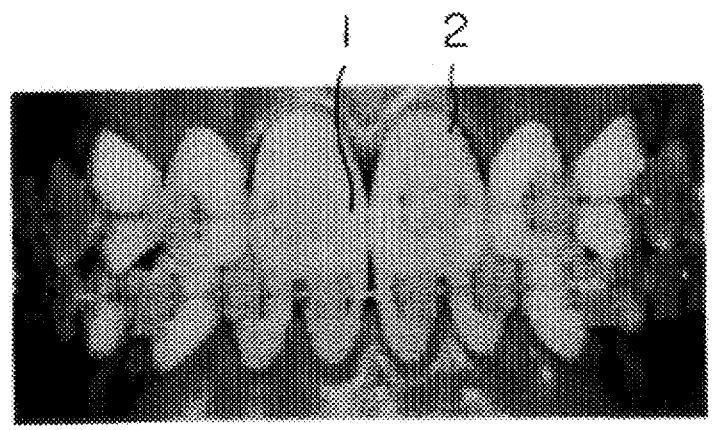
FIG. 1 is a photograph of an esthetic orthodontic wire according to the present invention, in a state to be actually installed to a teeth model.

According to the present invention, an esthetic orthodontic wire comprises a composite material including a biocompatible inorganic fiber(s), and a thermoplastic resin so that said wire is white and translucent, and excellent in estheticity.

The orthodontic wire is made of the composite material which is formed of the inorganic fiber having a biocompatibility and the thermoplastic resin (high polymer organic compound). The orthodontic wire preferably has a light transmittance of not lower than 5% to obtain an excellent estheticity. The "biocompatibility" means such a characteristics as to be harmlessly compatible to the tissue of an organism (living body) when the orthodontic wire is brought into contact with the organism tissue. The biocompatibility is experimentally evaluated by directly embedding a specimen of the orthodontic wire into the living body of an experiment animal and then observing whether abnormality arises or not in the tissue cells around the specimen. This will be discussed in detail in Example 1. The light transmittance represents a degree of transmittance of light through the specimen of the orthodontic wire and is measured as follows: The specimens of the orthodontic wire are arranged parallel and fixed to an inside surface of a specimen cell of a spectrophotometer. Pure water is poured into the cell. Then, the light transmittance is measured in a wet condition by using light rays within a visible light region. The orthodontic wire preferably has a light transmittance of not lower than 5% under light within the visible light region.

Examples of the biocompatible inorganic fiber of the orthodontic wire according to the present invention are disclosed, for example, in Japanese Patent Publication No. 62-12322 (U.S. Pat. No. 4,613,577), Japanese Patent Publication No. 1-30927 (U.S. Pat. No. 4,820,573), and Japanese Patent Publication No. 2-10244. Preferably, the inorganic fiber is glass fiber containing calcium and phosphate.

An example of the glass fiber containing calcium and phosphate is produced from a material (referred hereinafter as "CPSA") prepared by mixing calcium oxide, diphosphorus pentoxide, silicon dioxide and aluminium oxide. In order to improve the adhesiveness or bonding strength of the fiber to the thermoplastic resin during formation of the composite material, it is preferable that a surface treatment such as a so-called silane treatment.

Examples of the thermoplastic resin of the orthodontic wire according to the present invention are polymethyl methacrylate, polymethacrylate, polyacrylate, polyoxybenzoyl, polysulfone, polyethersulfone, polyetherether ketone, polyphenylene sulfide, polyimide, polyester carbonate, polyphenylene oxide, polyamide, polyacetal, polycarbonate, polybutylene terephthalate, polyethylene phthalate, fluorine-contained resin, polyethylene, polypropylene, polyethylene, and ABS resin. Of these resins, polymethyl methacrylate or a copolymer of methyl methacrylate and other methacrylate or acrylate is preferable for the material of the thermoplastic resin of the orthodontic wire according to the present invention because such resins are high in light transmittance and biocompatible. The thermoplastic resin preferably has a molecular weight within a range of from 10,000 to 1,000,000. Additionally, it is preferable from the view point of biocompatibility, that the thermoplastic contains ultraviolet ray absorbents, mould releasing agents, additives, stabilizers and the like are contained in an amount as smaller as possible.

The thermoplastic resin as a matrix is preferably high in light transmittance in order to improve the estheticity and coloring characteristics thereof upon being formed into the orthodontic wire. Accordingly, the light transmittance of the thermoplastic resin is not lower than 70%, preferably not lower than 80% and more preferably not lower than 90% under light within the visible light region in case that the thermoplastic resin is plate-shaped and has a thickness of 1 mm.

Thus, the orthodontic wire according to the present invention is biocompatible and high in light transmittance, and generally white and translucent (semitransparent). Additionally, the orthodontic wire hardly has its permanent set or deformation and can be formed such that an optimum orthodontic force required for an orthodontic cure can be freely set. The optimum orthodontic force is required and optimum for adjusting a dental arch or dentition. The optimum orthodontic force is represented by a load at a deflection of 1 mm, and is preferably within a range of from 0.5 to 6.0N which is lead from a value obtained by experience of using a known metal orthodontic wire. The value of this load corresponding to the optimum orthodontic force is affected by the content percentage (by volume) of the inorganic fiber in the orthodontic wire and measured under a so-called three-point flexural test according to JIS (Japanese Industrial Standard) K7055 in which the distance between supporting points is 14 mm; and the speed of the load is 1 mm/min. Under this test, a load-deflection curve is obtained, upon which the load and the flexural elastic modulus are calculated at the deflection of 1 mm. The above-mentioned content percentage of the inorganic fiber is obtained according to JIS K7052.

The inorganic fiber of the orthodontic wire according to the present invention has a diameter ranging from 1 to 100 μm, preferably 3 to 50 μm, and more preferably 5 to 30 μm. The inorganic fiber is formed continuous and is circular or oval in cross-section, in which the diameter or long diametrical dimension in the cross-section is within a range of from 3 to 30 μm, preferably 5 to 20 μm.

The content percentage of the inorganic fiber is controlled in conformity with an elastic modulus required for the orthodontic wire. This content percentage is generally 5 to 60% by volume, upon which the flexural elastic modulus falls within a range of from 16 to 42 GPa. In this connection, the value of the orthodontic force required for orthodontic cure can be freely controlled within a range of from 1 to 5N.

The above-discussed orthodontic wire according to the present invention offers the following advantages:

1) The biocompatibility of the above orthodontic wire according to the present invention is excellent as compared with that of conventional techniques. More specifically, conventional metal orthodontic wires provides the feeling of physical disorder to human's body. However, the orthodontic wire according to the present invention is preferably formed of a composite material including the glass fiber containing calcium phosphate, and therefore it is highly biocompatible.

2) The estheticity of the above orthodontic wire according to the present invention is further excellent as compared with conventional techniques. Accordingly, the patient himself or herself is free from anxiety, and therefore excellent cure effects can be expected. More specifically, if conventional metal orthodontic wires are used for orthodontic cure, unnatural metallic luster characteristic in the metal orthodontic wire is radiated from the orthodontic wire installed to the teeth of the patient thereby providing unpleasant feelings. However, the above-discussed orthodontic wire according to the present invention is formed of the composite material including the glass fiber containing calcium phosphate, and therefore it is white in external appearance thereby radiating soft reflected light similarly to human's natural teeth. This makes easy the external appearance of the teeth equipped with the orthodontic wire, providing excellent cure effects for the patient.

Figure 4:
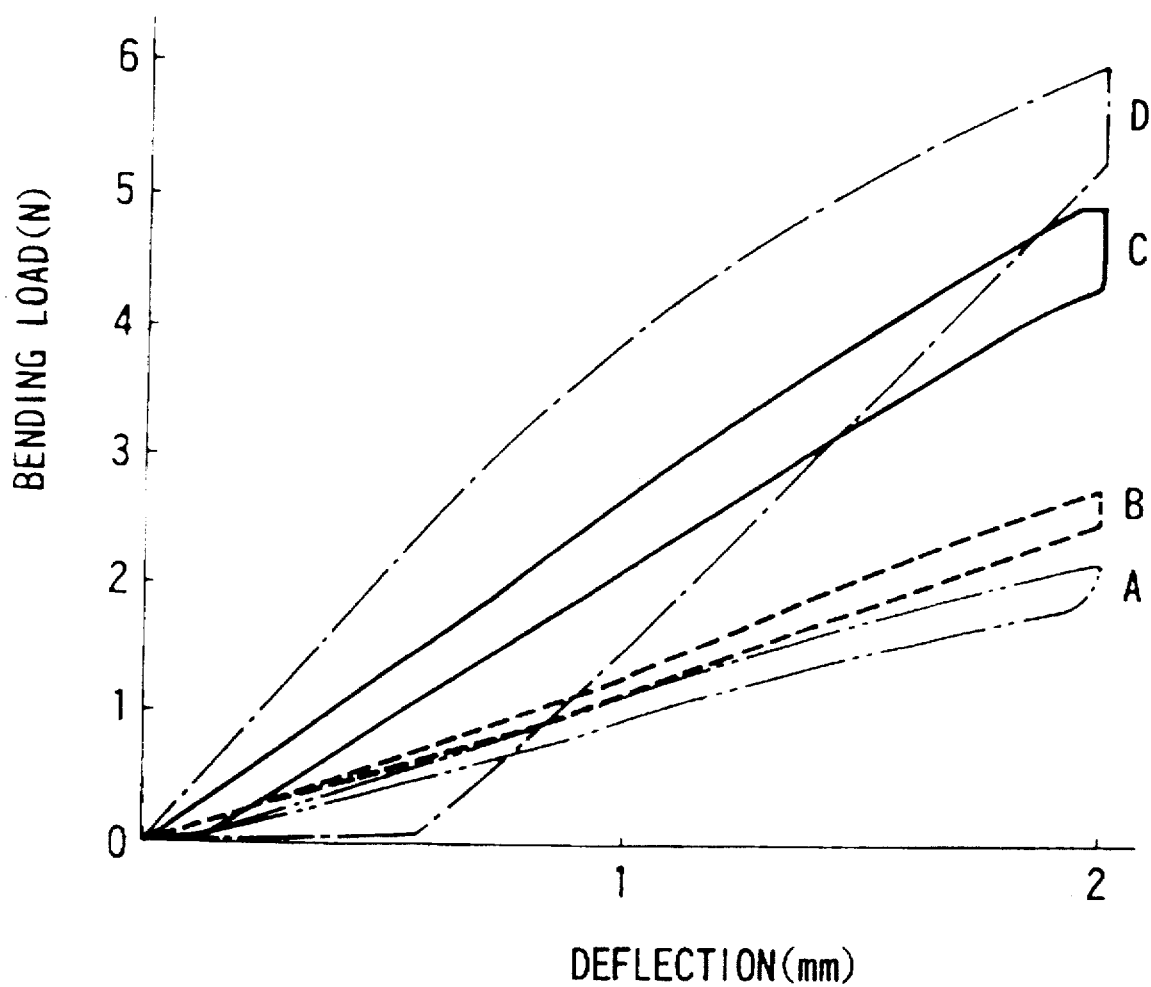
FIG. 4 is a graph showing the relationship between the bending load (N) and the deflection (mm) in connection with a variety of orthodontic wires.

3) In the orthodontic wire according to the present invention, when the load is returned to zero in the load-deflection curve, the deflection also returns to zero. This means that the material of the orthodontic wire hardly has its breakdown or yielding so that the force to be applied from the orthodontic wire to teeth cannot be lowered throughout a long time. In contrast, in a conventional Co—Cr wire for orthodontic cure, when the load is applied until the deflection reaches 2.0 mm and then returns to zero, the deflection of 0.6 mm is left as shown in FIG. 4. It will be understood that it is preferable that there is no such a residual deflection, exhibiting the zero level residual deflection. The thickness of the orthodontic wire has a circular or oval cross-section, in which the diameter or the long diametrical dimension in the cross-section is within a range of from 0.2 to 2.5 mm. In case that the orthodontic wire has a cross-section of regular square or rectangle, the short diametrical dimension in cross-section is within a range of from 0.2 to 5.0 mm. It will be understood that the cross-sectional shape of the orthodontic wire according to the present invention may circular, of regular square, rectangular, of braided rope, coloring can be made onto the orthodontic wire, in which the orthodontic wire is colored to be milk white or the like as to be in conformity with the color tone of the personal teeth. Additionally, the coloring the orthodontic wire may be made in conformity with the personal liking. The orthodontic wire according to the present invention may be formed of another composite material including an additional material(s) other than the thermoplastic resin and the glass fiber containing calcium phosphate. Examples of the additional material are metal, ceramic, and high polymer fiber.

4) The orthodontic wire according to the present invention is preferably formed of the composite material including the inorganic fiber and acrylic resin (as the thermoplastic resin) which is high in transparency and purity, in which the orthodontic wire can be so designed to have the optimum orthodontic force by changing the thickness of the inorganic fiber within a range of from 3.0 to 30 μm and the glass fiber content percentage within a range of from 5.0 to 70%.

EXAMPLE 1

1) Method of producing highly esthetic orthodontic wire

Law materials were mixed to form a glass material including 24.63 wt % of CaO, 17.48 wt % of P2O5, 33.39 wt % of SiO2 and 24.28 wt % of Al2O3. The glass material was supplied to a platinum crucible and heated for 3 hours to be molten in an electric furnace of which temperature was controlled at 1500° C. The thus molten glass material was got out from the crucible and broken. The broken glass material was again supplied into a platinum crucible which was formed at its bottom wall with a single hole having a diameter of 2.5 mm. The glass material was again heated in the crushable to be molten, in which glass flown out in the form of a single glass thread through the single hole of the crucible at a temperature of 1430° C. so that the flowing-out glass was continuously spanned at a speed of 450 m/min. by using a take-up device thereby obtaining the CPSA glass fiber having a fiber diameter of 20 μm. Then, the glass fiber was subjected to a coupling agent treatment, in which the glass fiber was dipped in a solution of γ-methacryloxypropyl triethoxysilane for 5 minutes. The glass fiber was taken out of the solution of the coupling agent and dried for 24 hours, and then subjected to baking for 5 minutes in a thermostatic oven. The CPSA glass fiber was well dispersed in a solution prepared by dissolving polymethylmethacrylate (having a molecular weight of 100,000 and produced by Mitsubishi Rayon Co., Ltd) in acetone, in which the CPSA glass fiber was impregnated with the solution. Then, the CPSA glass fiber was naturally dried and then subjected to a drawing fabrication using a glass die having an inner diameter of 0.5 mm which die was heated at 250° C. In order to control the glass fiber content percentage at 50% by volume in an orthodontic wire having a diameter of 0.5 mm, the bundle of the glass fiber was picked in a length of 32 cm and in a weight of 0.09 g.

(2) Measuring method of light transmittance

The fabricated orthodontic wiresss having a diameter of 0.5 mm and a glass fiber content percentage of 50% by volume were arranged and fixed on an inner surface of a rectangular (in section) liquid sample cell of a spectrophotometer in a manner that the path of light was perpendicular to the arranged wires. With this, the light transmittance was measured under light having wavelengths of 300 to 900 nm. The liquid sample cell was filled with pure water to measure the light transmittance which was represented in WET.

(3) Flexural test

The CPSA glass fiber was subjected to the three point flexural test, in which the distance between support points was 14 mm; and the speed of load is 1 mm/min.

The orthodontic wire which was prepared in the above manner was actually installed to a tooth arch model and compared in estheticity with a conventional metal orthodontic wire which was similarly installed to the tooth arch model.

Figure 2:
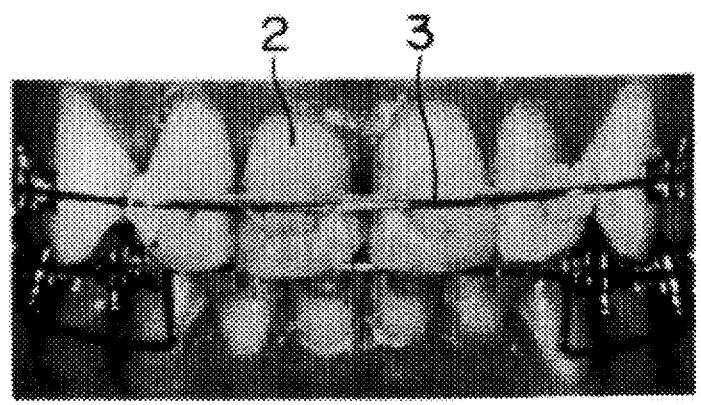
FIG. 2 is a photograph of a conventional metal orthodontic wire in a state to be actually installed to a teeth model.

FIG. 1 shows a case that the orthodontic wire according to the present invention was installed to the tooth arch model with a plastic bracket. FIG. 2 shows another case that the conventional metal orthodontic wire was installed to the tooth arch model with a plastic bracket. Comparison between FIGS. 1 and 2 demonstrated that the orthodontic wire (including the CPSA glass fiber) according to the present invention did not exhibit unpleasant luster characteristic for metal in the external appearance and therefore matched with natural teeth, so that the orthodontic wire was confirmed to be excellent particularly in estheticity.

Figure 3:
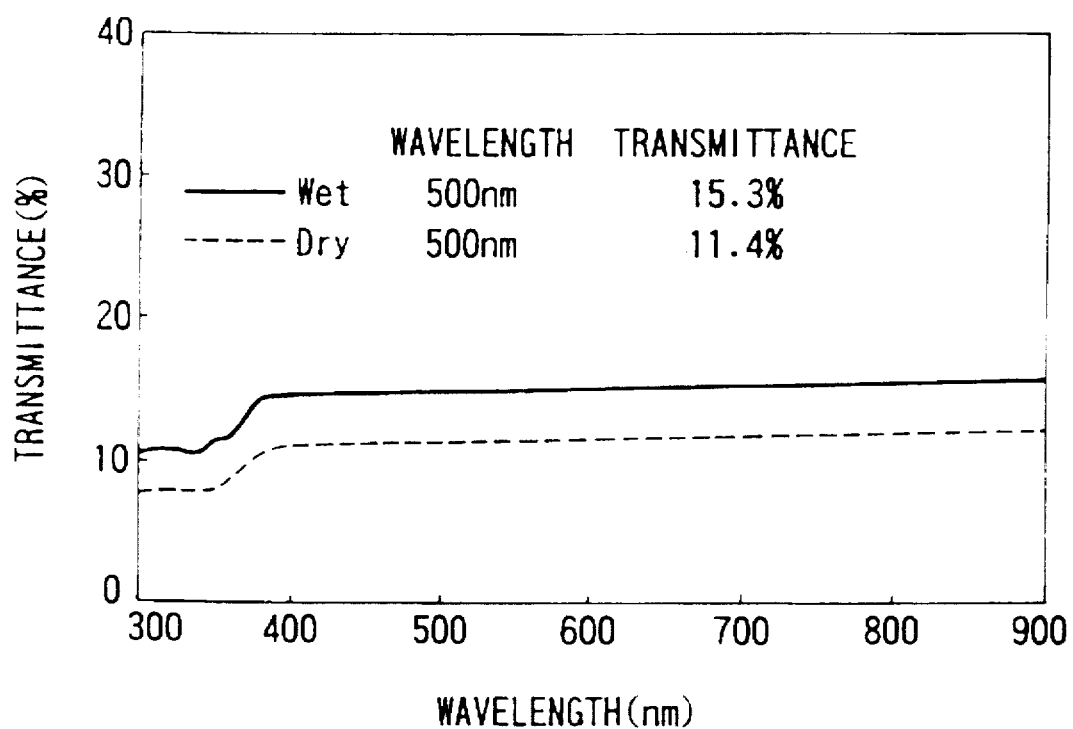
FIG. 3 is a graph showing the relationship between the light transmittance (%) and the wavelength (nm) of light in connection with the esthetic orthodontic wire according to the present invention.

FIG. 3 shows the result of measurement of light transmittance of the orthodontic wire (including the CPSA glass fiber) according to the present invention. In this measurement to obtain the relationship between the light transmittance (%) in vertical axis and the wavelength (nm) in horizontal axis, the orthodontic wire had a diameter of 0.5 mm, a fiber diameter of 20 μm, and an inorganic fiber content percentage Vf of 50% by volume. The measurement was made both in WET and DRY (no water was supplied in the sample cell). As a result, the light transmittance became generally constant at the wavelength of 400 to 700 nm in the visible light region both in the cases of WET and DRY, while the light transmittance was 15.3% in the case of WET and 11.4% in the case of DRY at the wavelength of 500 nm in the visible light region.

EXAMPLE 2

The biocompatibility of the orthodontic wire according to the present invention was evaluated as follows: A specimen having a diameter of 3 mm and a length of 10 mm was formed of the same material of the orthodontic wire used in Example 1, in which the diameter of the glass fiber was 20 μm; and the glass fiber content percentage was 50% by volume. This specimen was directly embedded in the base section of the femur of an adult dog. The specimen was taken out a plurality of times upon lapse of times to produce tissue specimens, in which a condition of tissue cells surrounding the specimen was observed by a microscope. As a result, the specimen embedded for about one year never provide abnormalities such as inflammation and appearance of huge cells while producing new bone around the specimen. This demonstrated that the orthodontic wire according to the present invention was good in biocompatibility with the living body.

EXAMPLE 3

The orthodontic wire (including CPSA glass fiber) was subjected to the three point flexural test, in which the glass fiber content percentage was changed to about 30% by volume, about 50% by volume, and about 60% by volume; and the distance between the support points was 14 mm. Conventional metal orthodontic wires were also subjected to the same three point flexural test for the purpose of comparison in performance. As shown in FIG. 4, the result of this test demonstrated that the orthodontic wire (indicated by B and C) according to the present invention exhibited load (bending load)-deflection behavior similar to those of the Ni—Ti system orthodontic wire (indicated by A) and the Co—Cr system orthodontic wire (indicated by D) which had been used nowadays for orthodontic cure. However, the Co—Cr system orthodontic wire exhibited a plastic deformation behavior characteristic for metal thereby holding a permanent deformation. This means that the Co—Cr system orthodontic wire had such a defect as to be low in orthodontic effect. In contrast, the orthodontic wires (indicated by C and B in FIG. 4) according to the present invention never exhibited a plastic deformation and exhibited only an elastic deformation so that no permanent deformation and no residual deflection were recognized. This means that the orthodontic wires according to the present invention can stably and continuously provide a constant orthodontic force to the teeth of the patient. The above experiments demonstrated that the orthodontic wires according to the present invention has desirable characteristics for orthodontic wire. It will be understood that the orthodontic wire according to the present invention can be designed to have a variety of the load-deflection behaviors by changing the diameter of the glass fiber and the glass fiber content percentage in the wire.

EXAMPLE 4

Figure 5:
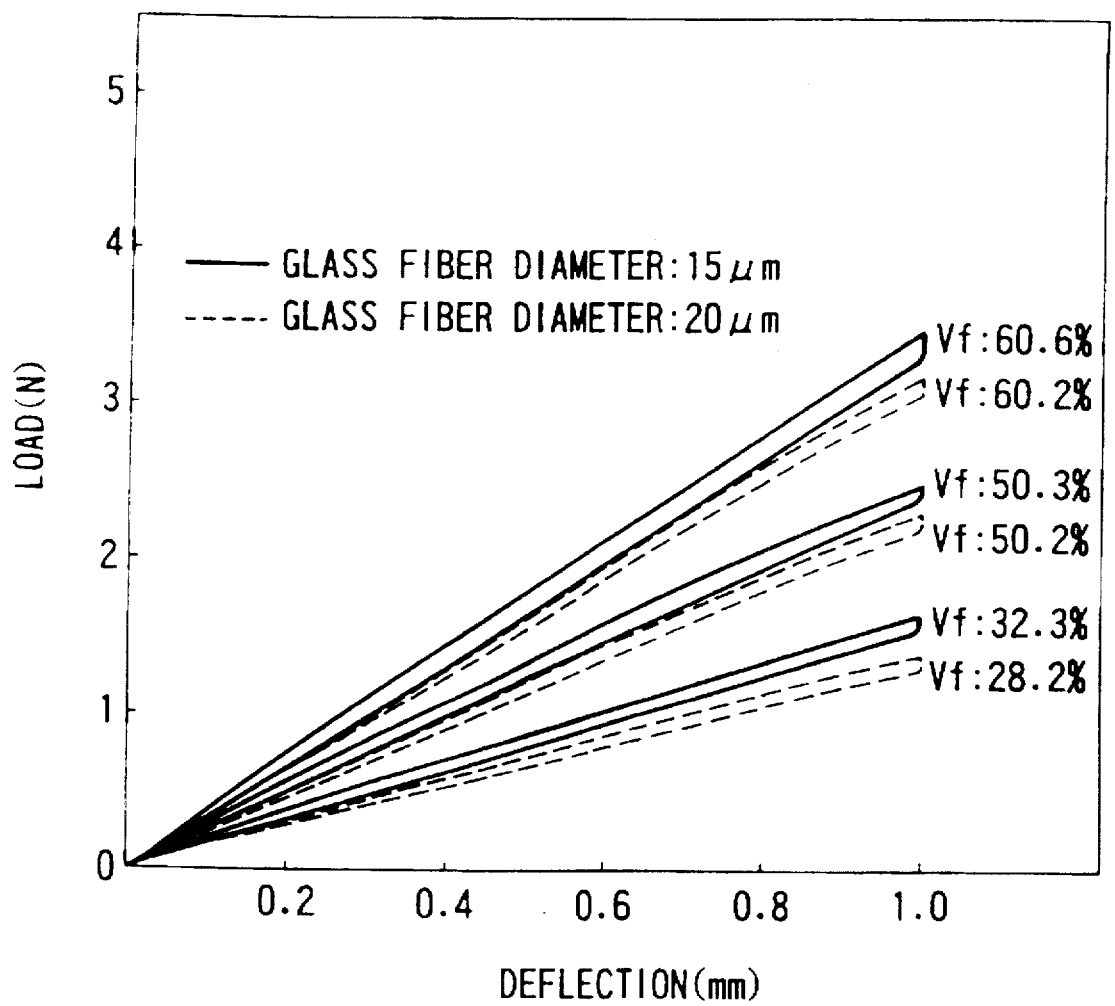
FIG. 5 is a graph showing the relationship between the load (N) and the deflection (mm) in connection with the esthetic orthodontic wire according to the present invention, illustrating the effects of glass fiber diameter and content percentage (by volume) of the glass fiber.

Effects of the glass fiber content percentage and the glass fiber diameter to the load-deflection behavior were experimentally confirmed for the orthodontic wire (including the CPSA fiber glass). More specifically, the load-deflection behaviors as shown in FIG. 5 were obtained by changing the glass fiber content percentage (Vf) as about 30 vol %, about 50 vol % and about 60 vol % and changing the diameter of the glass fiber as 15 µm and 20 µm. As a result, concerning effects of the deflection amount of 1 mm of the orthodontic wire, the load increased as Vf increased. The load was larger in the case of 15 µm of the glass fiber diameter than that in the case of 20 µm of the glass fiber diameter. This demonstrates that the orthodontic wire according to the present invention can be designed to have optimum orthodontic force necessary clinically for orthodontic cure by changing Vf, the glass fiber diameter and the diameter of the wire.

EXAMPLE 5

Frictional resistance of the orthodontic wire according to the present invention to a bracket in an orthodontic apparatus (not shown) was evaluated. More specifically, static coefficient µ of friction between the orthodontic wire and a bracket made of ceramic was measured, in which an orthodontic wire according to the present invention has a glass fiber diameter of 15 µm, a Vf value of 30% and a wire diameter of 0.5 mm; and a conventional Ni—Ti system orthodontic wire has a wire diameter of 0.46 mm. As a result, the orthodontic wire (including the CPSA glass fiber) according to the present invention had µ of 0.46, while the conventional Ni—Ti alloy system orthodontic wire had µ of 0.49. Thus, they had the generally same µ, and therefore it was confirmed that the orthodontic wire according to the present invention had no problem for clinical applications.

EXAMPLE 6

Flexural elastic modulus of the orthodontic wire (including the CPSA glass fiber) according to the present invention was measured for the orthodontic wire (including the CPSA glass fiber) according to the present invention which was drawing-fabricated to have a glass fiber content percentage (Vf) within a range of from 30 to 60% by volume and a wire diameter of 0.5 mm, in which the fiber diameter is 20 µm. As a result of this measurement, the orthodontic wire according to the present invention had a flexural elastic modulus within a range of from 16 to 42 GPa. Additionally, in the orthodontic wire according to the present invention, the load at the deflection of 1 mm in connection with the orthodontic force for adjusting the dental arch was within a range of from 1.2 to 1.8 N. Thus, with the orthodontic wire according to the present invention, it is possible to design an orthodontic wire having any load (or the orthodontic force) by changing the glass fiber content percentage (Vf). It was recognized that the orthodontic wire (including the CPSA glass fiber) according to the present invention had the generally same flexural elastic modulus and the load (at the deflection of 1 mm) as those of the conventional Ti—Ni alloy system orthodontic wire which had a diameter of 0.4 to 0.5 mm and had been nowadays practically used for orthodontic cure.

EXAMPLE 7

The orthodontic wire according to the present invention was subjected to a so-called in-vitro test since it was assumed that it came in contact with a variety of foods and drinks in mouth and changed in dynamic characteristics. The in-vitro test was conducted as follows: Specimens of the orthodontic wire according to the present invention were dipped respectively in an artificial saliva, pure water, a salad oil, a 20% ethanol solution, and a vinegar (1+2) solution, at 37° C. for 30 days. Thereafter, each specimen was subjected to the three point flexural test in which the distance between support points was 14 mm thereby measuring a flexural elastic modulus and the load at a deflection of 1 mm. The measured values of the flexural elastic modulus and the load were compared with the same values obtained before the dipping of the specimens so as to obtain retention percentage of the flexural elastic modulus and the load. Each specimen of the orthodontic wire had a glass fiber diameter of 20 µm and a Vf value of 50% by volume, a wire diameter of 0.5 mm. The flexural elastic modulus and the load of each specimen before the dipping were respectively 46.7 GPa and 3.1N (at the deflection of 1 mm).

(a) The retention percentage of the flexural elastic modulus and the load after the dipping in the artificial saliva were respectively 89% and 88%.

(b) The retention percentage of the flexural elastic modulus and the load after the dipping in the pure water were respectively 90% and 93%.

(c) The retention percentage of the flexural elastic modulus and the load after the dipping in the salad oil were respectively 98% and 98%.

(d) The retention percentage of the flexural elastic modulus and the load after the dipping in the 20% ethanol solution were respectively 98% and 99%.

(e) The retention percentage of the flexural elastic modulus and the load after the dipping in the vinegar (1+2) solution were respectively 70% and 73%.

Thus, it was recognized that change in dynamic characteristics of the orthodontic wire according to the present invention was not large after the orthodontic wire according to the present invention was in long contact with saliva and various foods and drinks. Even under a severe condition in which the specimen was continuously dipped in the vinegar solution for 30 days, the orthodontic wire according to the present invention had the retention percentage (in the dynamic characteristics) of about 70%, and the load (at the deflection of 1 mm) of 2.3 N which was in sufficient conformity with the optimum orthodontic force of about 0.1 to 3.0N.

What is claimed is:

1. An esthetic orthodontic wire comprising a composite material including a biocompatible inorganic fiber, and a thermoplastic resin, wherein the biocompatible inorganic fiber comprises a mixture of calcium oxide, diphosphorus pentoxide, silicon dioxide and aluminum oxide.

2. An esthetic orthodontic wire as claimed in claim 1, wherein said inorganic fiber is formed linearly continuous and has a generally circular or oval cross-sectional shape, said inorganic fiber having a diameter ranging from 1 to 100 µm.

3. An esthetic orthodontic wire as claimed in claim 1, wherein said inorganic fiber is biocompatible, in which a molar ratio of calcium/phosphorus is within a range of from 0.5 to 3.0, wherein total of calcium oxide and diphosphorus pentoxide is within a range of from 20 to 65% by weight relative to said glass fiber, and total of silicon dioxide and aluminium oxide is within a range of from 35 to 80% by weight relative to said glass fiber.

4. An esthetic orthodontic wire as claimed in claim 1, wherein content of said glass fiber is within a range of from 5 to 70% by volume of said orthodontic wire.

5. An esthetic orthodontic wire as claimed in claim 1, wherein said orthodontic wire has a generally circular or oval cross-sectional shape and has a diameter or long diametrical dimension within a range of from 0.1 to 5.0 mm.

6. An esthetic orthodontic wire as claimed in claim 5, wherein said orthodontic wire has a diameter or long diametrical dimension within a range of from 0.3 to 2.0 mm.

7. An esthetic orthodontic wire as claimed in claim 1, wherein said orthodontic wire has a generally regular square or rectangle cross-section, wherein said orthodontic wire has a short side in cross-section, within a range of from 0.1 to 5.0 mm, and a long side in cross-section, within a range of from 0.2 to 10.0 mm.

8. An esthetic orthodontic wire comprising a composite material including a biocompatible inorganic fiber, and a thermoplastic resin, wherein said orthodontic wire has a light transmittance of not lower than 5% within a visible light region.

9. An esthetic orthodontic wire as claimed in claim 1, wherein said thermoplastic resin is one selected from the group consisting of methylmethacrylate resin and a copolymer of methylmethacrylate and one of methacrylate and acrylate.

10. An esthetic orthodontic wire as claimed in claim 1, wherein said orthodontic wire has a residual deflection of not larger than 1 mm in a load-deflection behavior obtained under a test in which a distance between support points is 14 mm; and a flexural load is within a range of from 0.5 to 6.0 N.

11. An esthetic ortodontic wire comprising a composite material which includes:

a biocompatible inorganic fiber, said inorganic fiber being a glass fiber formed linearly continuous and having a generally circular or oval cross-sectional shape, said inorganic fiber having a diameter ranging from 1 to 100 μm, said biocompatible inorganic fiber being produced from a mixture of calcium oxide, diphosphorus pentoxide, silicon dioxide and aluminium oxide, said inorganic fiber being biocompatible, in which a molar ratio of calcium/phosphorus is within a range of from 0.5 to 3.0, wherein total of calcium oxide and diphosphorus pentoxide is within a range of from 20 to 65% by weight relative to said glass fiber, and total of silicon dioxide and aluminium oxide is within a range of from 35 to 80% by weight relative to said glass fiber, a content of said glass fiber being within a range of from 5 to 70% by volume of said orthodontic wire; and a thermoplastic resin which is one selected from the group consisting of methylmethacrylate resin and a copolymer of methylmethacrylate and one of methacrylate and acrylate;

wherein said orthodontic wire is geneally white and translucent, said orthodontic wire having a light transmittance of not lower than 5% within a visible light region, said orthodontic wire having a residual deflection of not larger than 1 mm in a load-deflection behavior obtained under a test in which a distance between support points is 14 mm; and a flexural load is within a range of from 0.5 to 6.0 N.

12. An esthetic orthodontic wire as claimed in claim 11, wherein said orthodontic wire has a generally circular or oval cross-sectional shape and has a diameter or long diametrical dimension within a range of from 0.1 to 5.0 mm.

13. An esthetic orthodontic wire as claimed in claim 12, wherein said orthodontic wire has a diameter or long diametrical dimension within a range of from 0.3 to 2.0 mm.

14. An esthetic orthodontic wire as claimed in claim 11, wherein said orthodontic wire has a generally regular square or rectangle, wherein said orthodontic wire has a short side in cross-section, within a range of from 0.1 to 5.0 mm, and a long side in cross-section, within a range of from 0.2 to 10.0 mm.

* * * * *